United States Patent
Milo

(10) Patent No.: US 8,393,517 B2
(45) Date of Patent: Mar. 12, 2013

(54) SURGICAL STAPLER AND METHOD OF SURGICAL STAPLING

(75) Inventor: Simcha Milo, Haifa (IL)

(73) Assignee: QuickRing Medical Technologies, Ltd., Haifa (IL)

(*) Notice: Subject to any disclaimer, the term of this patent is extended or adjusted under 35 U.S.C. 154(b) by 0 days.

(21) Appl. No.: 13/329,657

(22) Filed: Dec. 19, 2011

(65) Prior Publication Data

US 2012/0085809 A1    Apr. 12, 2012

Related U.S. Application Data

(63) Continuation of application No. PCT/IB2010/052804, filed on Jun. 21, 2010.

(60) Provisional application No. 61/269,664, filed on Jun. 26, 2009.

(51) Int. Cl.
*A61B 17/068* (2006.01)

(52) U.S. Cl. ........... 227/181.1; 227/82; 227/83; 227/85; 227/175.1; 227/19; 606/219

(58) Field of Classification Search .............. 227/82–83, 227/85, 175.1, 181.1, 19; 606/219
See application file for complete search history.

(56) References Cited

U.S. PATENT DOCUMENTS

| | | | |
|---|---|---|---|
| 4,317,451 A | 3/1982 | Cerwin et al. | |
| 4,396,139 A * | 8/1983 | Hall et al. ........................ | 227/19 |
| 4,485,816 A | 12/1984 | Krumme | |
| 4,505,273 A | 3/1985 | Braun et al. | |
| 4,676,245 A | 6/1987 | Fukuda | |
| 5,413,584 A | 5/1995 | Schulze | |
| 5,544,802 A * | 8/1996 | Crainich ..................... | 227/176.1 |
| 5,695,504 A * | 12/1997 | Gifford et al. ................ | 606/153 |
| 6,203,553 B1 | 3/2001 | Robertson et al. | |
| 6,451,034 B1 * | 9/2002 | Gifford et al. ................ | 606/153 |
| 6,524,338 B1 | 2/2003 | Gundry | |
| 6,702,826 B2 | 3/2004 | Liddicoat et al. | |
| 6,913,608 B2 | 7/2005 | Liddicoat et al. | |
| 7,004,958 B2 | 2/2006 | Adams et al. | |
| 7,037,334 B1 | 5/2006 | Hlavka et al. | |
| 7,229,452 B2 * | 6/2007 | Kayan .......................... | 606/142 |
| 7,473,258 B2 | 1/2009 | Clauson et al. | |
| 7,485,142 B2 | 2/2009 | Milo | |
| 2003/0171776 A1 | 9/2003 | Adams et al. | |
| 2005/0096660 A1 * | 5/2005 | Allen .............................. | 606/75 |
| 2005/0283190 A1 | 12/2005 | Huitema et al. | |
| 2010/0268253 A1 | 10/2010 | Ahlberg et al. | |

FOREIGN PATENT DOCUMENTS

| | | |
|---|---|---|
| EP | 1 870 042 B1 | 12/2007 |
| WO | 97/12729 A2 | 4/1997 |

* cited by examiner

*Primary Examiner* — Brian D Nash
*Assistant Examiner* — Michelle Lopez
(74) *Attorney, Agent, or Firm* — Fitch, Even, Tabin & Flannery LLP

(57) ABSTRACT

Surgical stapling methods and tools which allow a surgeon to create several different predetermined amounts of tissue constriction using the same staple (11) loaded in such a tool (31). A stapling tool (31) holding one or more staples in an effector section (35) contains a mechanism for spreading the pointed ends of a staple to one of several spaced apart distances as controlled by an actuator-indicator (43). Depending upon the distance the pointed ends have been spread when the staple is implanted into tissue (51), the amount of constriction accomplished by the staple is varied. An improved staple construction (61) of increased rigidity is also shown.

17 Claims, 5 Drawing Sheets

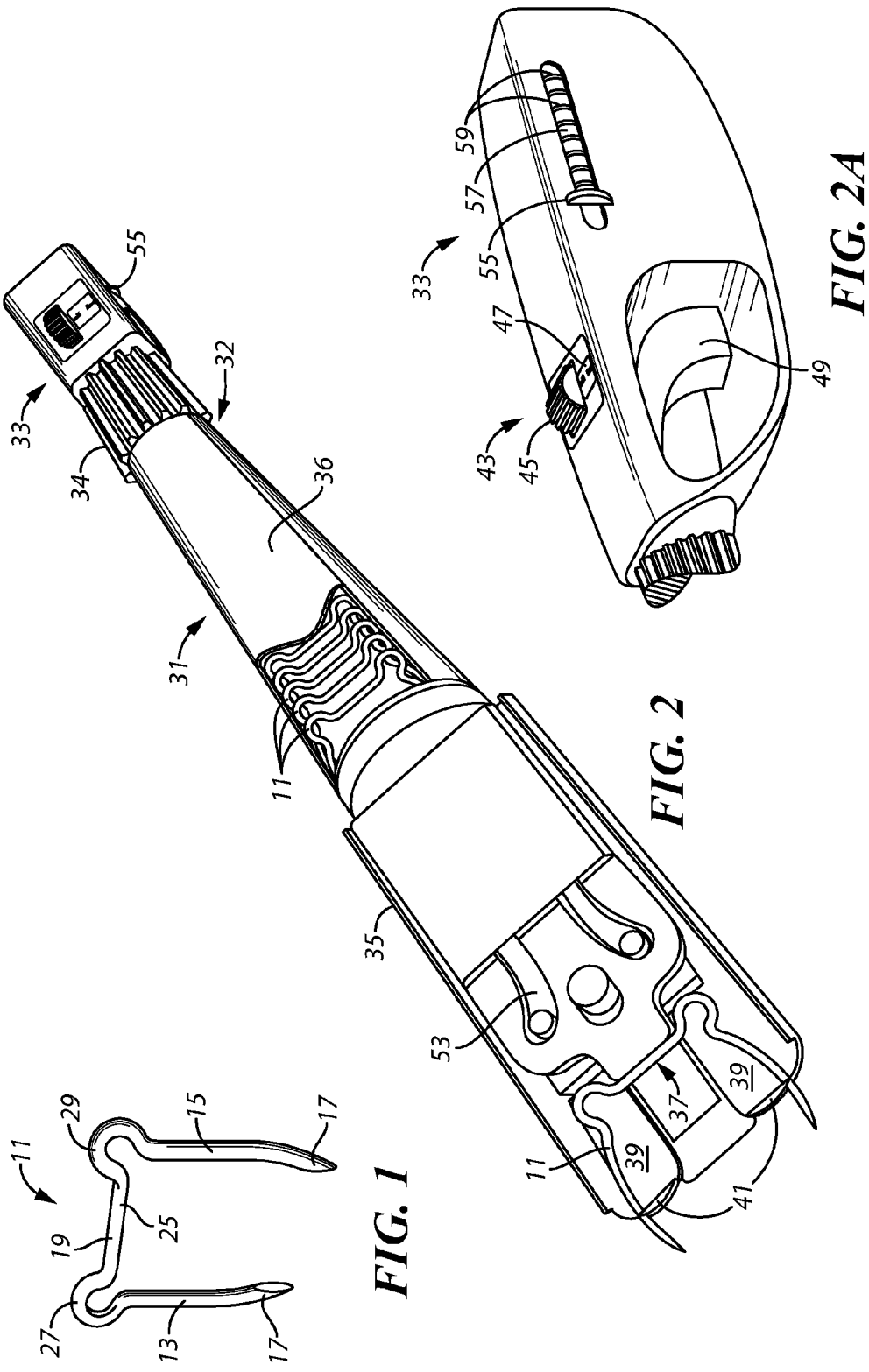

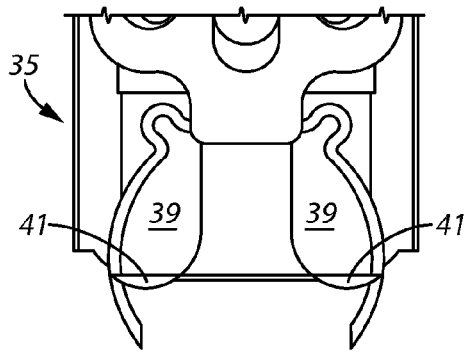
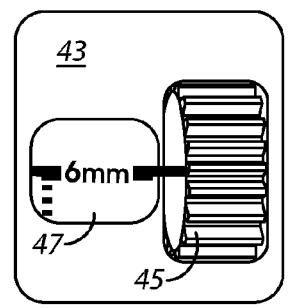
*FIG. 3*  *FIG. 3A*
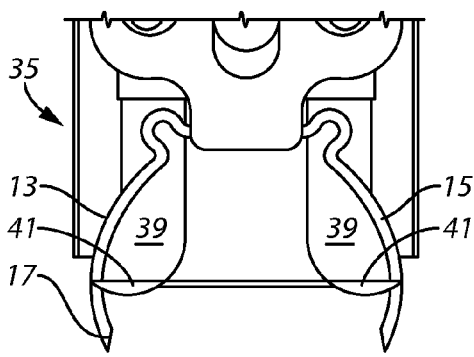
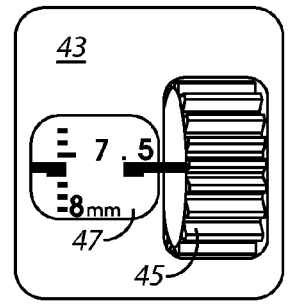
*FIG. 4*  *FIG. 4A*

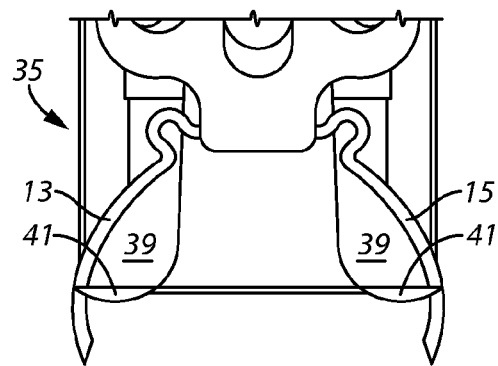
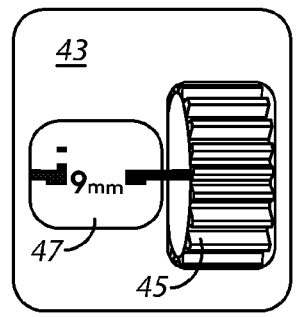
FIG. 5  FIG. 5A
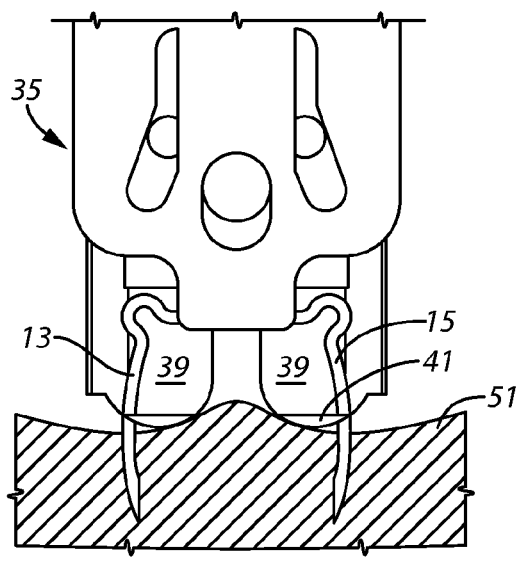
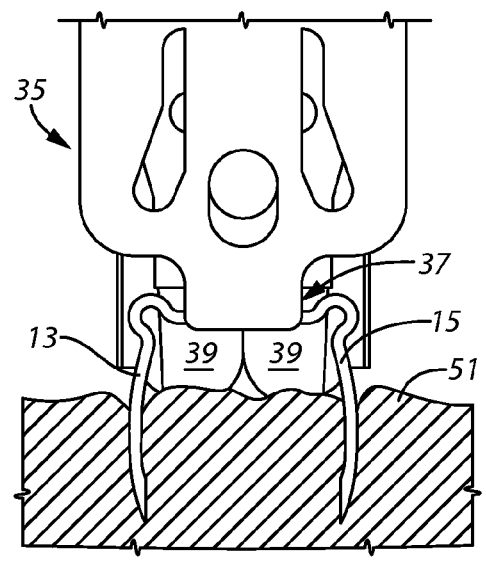
FIG. 6  FIG. 7

SURGICAL STAPLER AND METHOD OF SURGICAL STAPLING

CROSS REFERENCE TO RELATED APPLICATIONS

This application is a continuation of International Application PCT/IB2010/052804, filed Jun. 21, 2010, which claims priority from U.S. Provisional Application Ser. No. 61/269,664 filed Jun. 26, 2009, the disclosures of both which are incorporated herein by reference.

FIELD OF THE INVENTION

This invention relates to surgical stapling, and more particularly to tools for effecting surgical stapling, to methods of surgical stapling and to an improved staple construction.

BACKGROUND OF THE INVENTION

Although suturing has traditionally been used to join tissue and close wounds, in recent years, surgical stapling has begun to supplant suturing because of the time-saving afforded and because less skill is generally required to effect surgical stapling as a result of the availability of tools which are consistent in precise implantation of a surgical staple. Surgical staples have been used not only to join portions of tissue to close a wound or the like, but to affix a prosthesis to tissue, as in annuloplasty operations, for example.

The patent art is replete with a plethora of U.S. patents showing a wide variety of surgical staples made both of shape-memory material and of non-shape memory material which undergoes plastic, i.e. non-reversible, deformation in order to effect joinder or constriction of tissue. It is also replete with tools or devices for implanting such staples into body or organ tissue which may be used to effect such methods of tissue joinder and/or constriction using such surgical staples. Examples of such are found in the following U.S. patents and published applications: U.S. Pat. Nos. 4,485,816; 4,505,273; 5,413,584; 6,702,826; 6,913,608; 7,037,334; 7,473,258; 7,485,142 and U.S. Published Application Nos. US 2003/0171776 and US 2005/0283190.

The multitude of patents in this art show that improvements have long been sought, and the search for improved methods of surgical stapling continues.

SUMMARY OF THE INVENTION

The invention provides methods for using a single staple to effectively create several different amounts of constraint within tissue into which the staple is implanted. Stapling tools are provided which manipulate a staple of a given size and shape so as to allow a surgeon to obtain several different degrees of constraint in tissue once the staple has been implanted.

In one more particular aspect, the invention provides a surgical stapling tool which comprises a main body which includes a handle portion, an effector extending from said body which holds at least one surgical staple having two legs with pointed ends and a crown connector interconnecting the opposite ends of the legs, said effector including a first mechanism for adjusting the distance between the pointed ends of the legs so they become spaced apart a precise desired distance that is one of several different distances, an actuator-indicator incorporated in said body for operating said first mechanism, a second mechanism which causes the effector to implant the staple into body tissue or organ tissue so as to achieve a precise amount of constriction, which constriction is dependent upon the one of said several different precise spaced apart distances to which the pointed ends were adjusted, and an actuator for causing said second mechanism to operate.

In another particular aspect, the invention provides a method of surgical stapling which comprises the steps of providing a stapling tool which holds at least one surgical staple having two legs with pointed ends and a crown connector interconnecting the opposite ends of said legs, with the pointed ends spaced an initial distance apart, manipulating the tool to change the distance between the pointed ends of said legs so they are now spaced apart a precise desired distance which is different from said initial distance, and then causing the tool to implant said staple into body or organ tissue so as to achieve a precise amount of tissue constriction dependent upon said precise spaced distance to which the pointed ends were set by said manipulating step.

In a further particular aspect, the invention provides a method of constricting a region of body or organ tissue by surgical stapling which method comprises the steps of (1) providing a stapling tool which is loaded with at least one surgical staple having two legs with pointed ends and a crown connector interconnecting the opposite ends of the legs, with the pointed end spaced an initial distance apart, (2) manipulating the tool to change the distance between the pointed ends of the legs so they are spaced apart one of several precise distances, which are different than said initial distance, and (3) then using the tool to implant the staple into the body or organ tissue so that, as a result of such implantation, the staple achieves a precise amount of constriction in the tissue dependent upon to which of said precise spaced distances the pointed tips of the legs were adjusted.

In a still further particular aspect, the invention provides a surgical staple which comprises two legs having pointed free ends and a crown connector interconnecting the upper ends of said legs, said staple being essentially planar and formed completely of wireform material having an I-beam cross-section where two parallel flanges flank a central web, which flanges are oriented perpendicular to the plane of the staple.

BRIEF DESCRIPTION OF THE DRAWINGS

FIG. 1 is a perspective view of a staple that might be used with this stapling method.

FIG. 2 is a perspective view of a surgical stapling tool illustrated schematically, with portions broken away, with the staple of FIG. 1 mounted therein and showing the pointed tips of the staple spaced apart at an initial minimal distance of, for example, 6 millimeters (mm).

FIG. 2A is an enlarged, fragmentary, side perspective view showing the actuator-indicator portion of the tool of FIG. 2.

FIG. 3 is a fragmentary top view, enlarged in size, of the stapling tool as shown in FIG. 2.

FIG. 3A is a top view of the actuator-indicator portion atop the handle of the tool of FIG. 2.

FIG. 4 is a fragmentary front view, similar to FIG. 3, wherein the stapling tool has been manipulated so as to adjust the legs of the staple so the pointed tips are spaced apart at a greater predetermined distance, e.g. about 7.5 mm.

FIG. 4A is an enlarged fragmentary view similar to FIG. 3A showing the actuator-indicator portion of the tool as adjusted for FIG. 4.

FIG. 5 is a fragmentary front view similar to FIG. 4 wherein the stapling tool has been manipulated so as to adjust the legs of the staple so the pointed tips are spaced apart at a still greater predetermined distance, e.g. 9 mm.

FIG. 5A is an enlarged fragmentary view similar to FIG. 3A showing the actuator-indicator portion of the tool as adjusted for FIG. 5.

FIG. 6 is a schematic view showing the stapling tool of FIG. 3 as the pointed tips of the staple have been caused to initially enter the tissue, the surface of which is momentarily deformed downward by the entry of the pointed tips.

FIG. 7 is a view similar to FIG. 6 where the staple has its legs implanted further into the tissue and where the arms of the tool that were used to spread the legs to the desired spaced apart distance have been withdrawn to a central location.

DETAILED DESCRIPTION OF THE PREFERRED EMBODIMENTS

Figure 8:
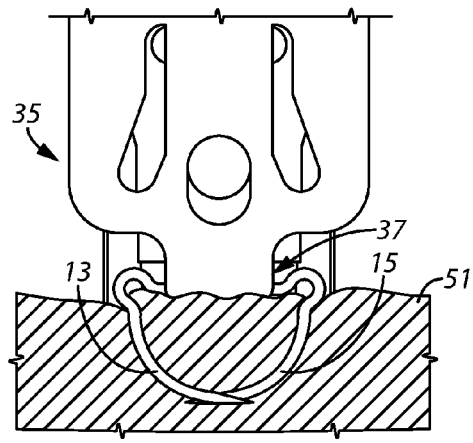
FIG. 8 is a schematic view similar to FIG. 6 wherein the staple has been inserted into the tissue so that the crown connector of the staple is now juxtaposed with the tissue surface and with the staple tool effector still in contact with the crown connector while the legs of the staple have closed.

Illustrated in FIG. 1 is a staple 11 that might be loaded in a surgical stapling tool and employed in a surgical stapling method which embody various features of the invention. The staple 11 includes a pair of legs 13,15 which depend from a crown connector 19. The legs have pointed lower ends 17 and are respectively connected to the crown connector at the bottom of a pair of ears 27,29, each of which is a loop of about 270 degrees that is integral with a central linear bar section 25 of the crown connector. The ears 27,29 are preferably integral with both the bar connector and the legs, as the staple 11 is preferably formed from an integral piece. Each leg of the staple embodiment illustrated in FIG. 1 is formed with a shallow curvature, with the concave surfaces facing each other.

Although the embodiment of the staple illustrated in FIG. 1 is planar, the method is not restricted to using such staples. For example, illustrated in pending International Publication No. WO 2009/130631 are a variety of staples which are designed to interlock with one another. These other embodiments of surgical staples include rings extending from one or both sides of the staple through which a leg of an adjacent staple would be passed. Also included are surgical staples which instead of having a straight planar center section in the crown connector are formed with an undulating section designed to provide some resiliency.

It can be seen that the legs 13,15 are spaced apart a fixed distance at their upper ends where they are integral with the crown connector 19; this distance does not change upon implantation. However, as a part of the stapling method, the distance at which the pointed ends 17 are spaced apart is adjusted while the staple 11 remains loaded in the stapling tool. The tool is designed so that the surgeon can manipulate it so as to space the pointed staple ends 17 apart at several different predetermined distances. By varying the spacing of the pointed ends 17 of the legs of the staple being delivered to the tissue, the pointed ends will pierce the tissue at different distances, whereas the upper ends of the two legs will be spaced apart a predetermined distance. Once below the surface of the tissue, the legs 13,15 are caused to bend or curve toward each other, and in this manner, they gather the tissue in the region below the surface and effect a constriction of the tissue in a direction defined by the linear connector bar 25.

The movement of the two legs 13,15 toward each other can be the result of a shape-memory attribute of the metal from which the surgical staple is fabricated as illustrated in FIGS. 5-8. Alternatively, it can be the result of the action of the delivery tool effecting plastic deformation of the staple itself after the tips have pierced the tissue and while the implantation of the staple is progressing. The staple construction is such that the illustrated linear connector bar 25 (or a non-linear equivalent such as mentioned above) will usually lie in juxtaposition with the tissue surface, with major portions of the ears 27,29 also lying above the surface. Accordingly, all of the change in shape of the staple 11 occurs in the legs 13,15, after they are implanted or embedded in the tissue; the movement of the two legs toward each other very effectively constricts the region of the tissue below the crown connector 19 and results in tightening the crown connector to the tissue. The extent of the constriction is determined by the extent to which the pointed ends 17 of the staple were spread apart by the stapling tool; thus, the greater distance the pointed ends 17 are spread apart, the greater will be the constriction of the tissue in this region. Reference to the following description and the accompanying Figures will render this concept quite clear.

The surgical staples 11 may be made from a suitable biocompatible, likely metal alloy, material; standard surgical staple materials include biocompatible metals, such as titanium alloys, nickel-chromium alloys and clad stainless steels. Alternatively, the staples may be made of a material having shape-memory characteristics, such as nitinol or other similar biocompatible nickel-titanium alloys. They may also be made of layered metals where one metal is sandwiched between two others to provide a composite material, and such may include memory and non-memory superelastic alloys and metals. Temperature-dependent nitinol, a Ni—Ti alloy containing about 50.6 to 51.0 atomic % nickel that will return to a preset shape once the surgical staple warms to body temperature, is a commonly chosen shape-memory material. Alternatively, one of the so-called superelastic materials might be used, e.g. another nickel-titanium alloy, a cold drawn stainless steel or some other biocompatible, spring-like metal alloy that has been appropriately treated. For example, the staple may be formed and treated to give it a predetermined final set shape to which it will return; then it is deformed without harm to a delivery shape for implantation where the two legs are spaced apart from each other as seen in FIGS. 3-5. The elasticity or springback of nitinol is many times greater than other shape-memory materials.

When not made from such shape-memory materials, the surgical staples may be made from such biocompatible metals well known in this art that have been used for decades for surgical staple manufacture and which have been found to have a long lifetime in the human body without corrosion/absorption/degradation or cause of undesirable side effects. When such non-memory materials are used for fabrication of the surgical staples, a delivery device is employed that applies forces to the legs at locations below their upper ends to cause the two legs (which have been just spread apart to a desired predetermined distance) to now bend or preferably curve toward each other at locations below the tissue surface and thereby securely gather tissue between the two approaching legs and create a constriction of a predetermined amount, e.g. 2 to 4 mm in the tissue below its upper surface, in the direction defined by the crown connector, e.g. in the plane of the rigid, linear connecting bar 19 and the legs 13 and 15.

FIG. 2 illustrates a surgical stapling tool 31 having a main body 32 that includes a handle portion 33, a central rotatable barrel portion 34 that includes a knurled knob to facilitate rotation to the desired orientation and an effector 35 portion which extends distally from the main body and holds at least one staple 11 as illustrated. A transparent sheath (not shown) may cover a portion or all of the front face of the effector portion. In accordance with principles well-known in the stapling art, the tool 31 can be designed to be loaded with a removable cartridge 36 of staples so that, after implanting a single staple, the effector 35 is reloaded with the next staple at the end of the cartridge 36 after the effector has been withdrawn from implanting a staple. The staple 11 is received in a holder 37 that forms a part of the effector and has a groove 38 (see FIG. 9) which receives the central region of the crown connector (e.g. a linear groove which accepts the linear bar section 25 of the crown connector 19). Alternatively, a new staple 11 may be manually loaded after each implantation instead of employing such a cartridge. Such an alternative would simplify the tool and the operation. Two such tools might be employed with the scrub nurse reloading one with a new staple as the surgeon is implanting each staple.

The effector 35 has a pair of arms 39 that are juxtaposed with the rear surface of the holder 37 and extend distally therefrom. Each arm has a finger 41 which is formed on the front face of the distal end of the arm, and which extends laterally outward at about a right angle to the arm. This finger 41 creates a shallow pocket between the finger 17 and the front flat surface of the arm 39 wherein the slightly concave interior surface of one of the legs 13,15 of the staple is seated in its initial loaded shape wherein the pointed ends 17 are separated by a predetermined distance of, for example, 6 mm (see FIGS. 2 and 3). The tool 31 includes an actuator-indicator 43 which is incorporated in the handle portion 33 of the main body on the upper surface thereof and which, upon turning a knurled thumbwheel 45 or the like, effects separating movement of the arms 39 to which the thumbwheel is mechanically linked; the amount of deformation is indicated on a micrometer-like readout or scale 47. Lateral separation of the arms 39 causes the protruding finger 41 pockets to press against the interior surfaces and spread the legs 13,15 of the loaded staple further apart from each other. Once the desired spacing has been set for that staple, actuation by pulling a trigger 49 a first amount initiates the staple implantation action of the spring-loaded effector.

FIGS. 3 and 3A are enlarged views of portions of the tool with the staple loaded with its legs separated by the predetermined initial distance, e.g. 6 mm. FIGS. 4 and 4A show the addition of a first additional increment of spacing by spreading the legs a greater predetermined distance apart, i.e. where the pointed ends 17 of the legs are now spaced apart about 7.5 mm. FIGS. 5 and 5A show further adjustment to add a second still greater increment of spacing, where the pointed ends 17 are now spread apart to a predetermined distance of about 9 mm.

To illustrate the method implantation of a staple 11 by the surgical stapling tool 31, reference is made first to FIG. 6, wherein there is depicted the loaded stapling tool of FIG. 3 with the pointed ends 17 of a shape-memory staple spread apart to a distance of about 6 mm. the stapling action may be initiated by pulling the trigger 49 an initial amount to release the spring-loaded effector. The staple is shown being inserted into tissue 51 for the purpose of creating a constriction of such tissue, as might be desired in an annuloplasty operation like that described and claimed in U.S. Pat. No. 7,485,142. From FIG. 6, it can be seen that pointed ends 17 of the legs of the staple enter the tissue 51 at the spaced-apart distance as set by the finger 41 pockets at the distal ends of the two arms 39 wherein the slightly concave facing interior surfaces of the legs are seated. The fingers 41 provide such shallow pockets that are used to spread the legs a precise distance apart from each other so that the pointed tips are spaced apart to one of several different predetermined distances to meet the desire of the surgeon for this particular staple in order to achieve a localized greater or lesser amount of constriction. The tissue 51 is momentarily locally deformed downward by the entry of the tips 17 as depicted in FIG. 6.

FIG. 7 illustrates the tool 31 with the arms 39 having now been quickly manipulated to be moved closer together so as to remove contact between the fingers 41 and the legs 13,15 of the staple. Camming slots 53 may be used to control the action of the arms 39 as generally schematically shown. Some further movement of the tool 31 distally to implant the staple 11 more deeply in the tissue 51 is also depicted in FIG. 7. At this time, the fingers 41 may also be withdrawn slightly rearward so they no longer reside within the plane of the staple 11, or such withdrawal movement can be delayed until the crown connector 19 is juxtaposed with the tissue surface and has become tightened thereagainst.

FIG. 8 schematically represents the tool 31 where the holder 37 has reached the surface of the tissue 51, and the staple 11 has been fully implanted. The fingers 41 may have been withdrawn rearward by this time if desired. Furthermore, sufficient time is depicted as having elapsed such that the legs 13,15 have become curved toward each other, generally remaining within the plane of the staple, to provide the crimped orientation with the now arcuate, distal portions of the two legs lying side-by-side. As a result of the movement of the legs 13,15 approaching each other below the tissue surface, the tissue 51 in which the staple 11 was implanted becomes crimped in this location, constricting the tissue and, if performed in an annuloplasty, shortening the valve annulus and thus tightening the valve against leakage.

Figure 9:
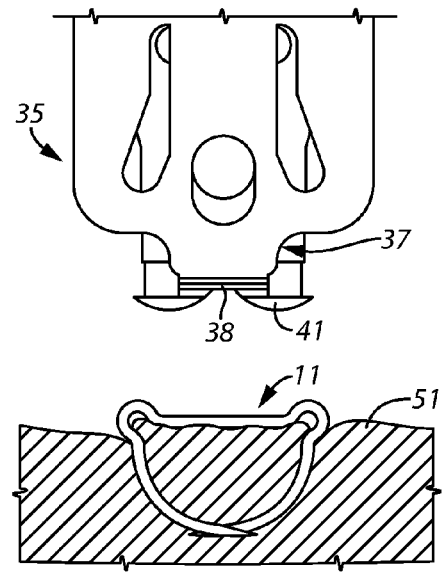
FIG. 9 is a view similar to FIG. 8 showing the stapling tool disengaged from the implanted staple and being withdrawn.

The sequence illustrated in FIGS. 6-8 is generally representative of the implantation of a superelastic material staple that has its shape-memory set to return to its pre-set constricting configuration shown in FIGS. 8 and 9. Thus, it should be apparent that, dependent upon the greater the amount of distance between the pointed ends (to which the tool 31 has spread apart the pointed tips 17 of the legs), the greater will be the amount of constriction of the tissue 51 achieved by the implanted staple once it has returned to its preset configuration which is now shown in FIG. 8. The strong springback properties of superelastic nitinol, stainless steel and like metal alloys make them well suited for this application.

FIG. 9 is a representation of the removal of the surgical stapling tool 31 from its connection with the now implanted staple 11. The holder portion of the tool is moved slightly rearward to disengage the linear bar 25 from the slot or groove 38 in the holder 37 when the trigger 49 is pulled back to its final rear position, and the fingers 41 are withdrawn from between the crown connector 19 and the tissue surface if they were not earlier withdrawn. In FIG. 9, the slot or groove 38 in the holder 37 where the central rectilinear bar section 25 was disposed can be seen. The barrel 34 of the tool is preferably made rotatable to the handle 33 so that the surgeon can more easily orient the plane of the staple 11 about to enter the tissue 51 to the orientation so as to attain the desired direction of constriction and the angle of deployment. In the illustrated tool 31, it is contemplated that the spring-load effector 35 would be manually reset for the next implantation; for example, a button 55 that slides in an elongated slot 57 could be pulled rearward by one's thumb to load a compression spring 59.

Figure 10:
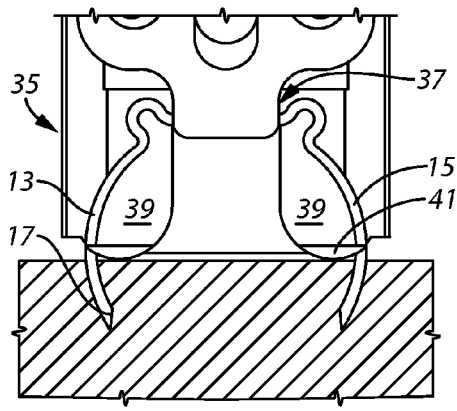
FIG. 10 is a view of the tool and staple of FIG. 4, showing the pointed tips of the staple just piercing the tissue.
Figure 11:
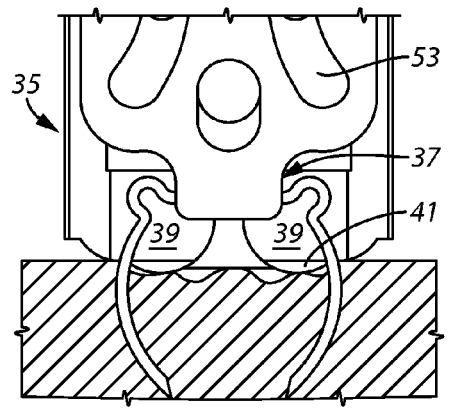
FIG. 11 is a view similar to FIG. 10, showing deeper implantation of the staple and some bending movement of the staple legs to constrict the tissue below the surface thereof.

FIG. 10 is a schematic view, generally similar to FIG. 6; it shows the pointed tips 17, of the staple 11 that was loaded in the holder 37 of the stapling tool, after having been extended to a greater predetermined spaced apart distance, now beginning to pierce the surface of the tissue into which implantation is occurring. FIG. 11 is a view of the FIG. 10 arrangement showing a further stage of the implantation where the fingers 41 have now been moved toward each other, so the interior surfaces of the legs 13,15, so the legs are no longer seated in the shallow pockets. The legs are shown as having begun to curve inward toward each other as the downward implantation movement of the holder nears the end of its stroke.

Although the schematic representations shown in FIGS. 6-9 depict the implantation of a staple 11 made of shape-memory material, it should be understood that the implantation tool can be modified to avail itself of techniques common in surgical stapling tools that will cause the legs of a non-shape memory material staple to undergo plastic deformation after the tips have pierced the tissue to a desired depth and, as a result, achieve substantially the same implanted staple constricting configuration as that shown in FIGS. 8 and 9. By plastic deformation is meant the deformation of a metal alloy or other material that is caused to be permanently deformed as a result of having been subjected to a stress that exceeds its yield value. It can be understood that such staples, as a prelude to the implantation, would be subjected to elastic deformation by spreading the legs further apart; however, if staples of non-shape memory materials are being used, subsequent mechanisms of the surgical stapling tool following the pointed ends piercing the tissue, are designed to cause the legs to reach the orientation depicted in FIGS. 8 and 9, during the course of which, the legs would be subjected to plastic deformation so that they would remain in this shape once the stress has been removed.

As previously indicated, the staples may have a variety of different shapes so long as they include a pair of preferably shallow concave legs that are essentially planar and that extend distally from a crown connector. The desired result is that all of the constriction occurs below the surface of the tissue that has been pierced. While the presence of the 270 degree ears is preferred and might be used to accommodate a bar section of a fenestrated annuloplasty ring such as shown in the '142 patent, or to effect interlocking to create a chain of constricting staples, as also shown in the '631 published international application, such ears might be modified or even eliminated if desired.

Figure 12:
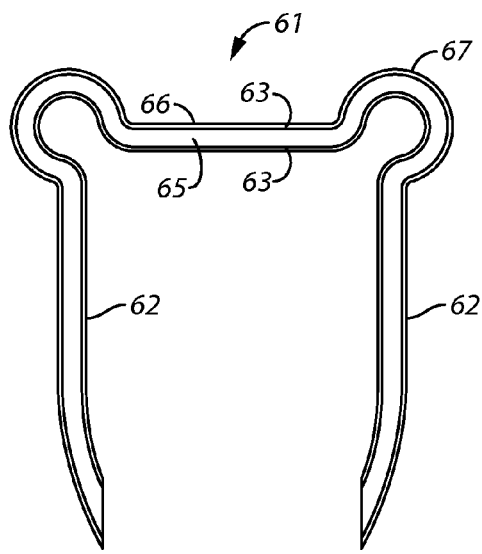
FIG. 12 is a front view of an alternative embodiment of a staple.
Figure 13:
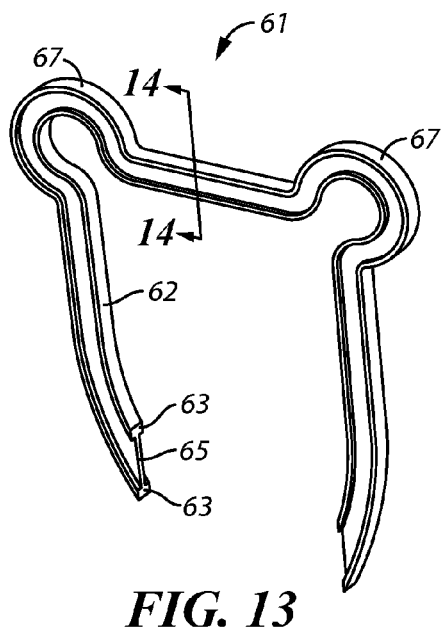
FIG. 13 is a perspective view of the staple shown in FIG. 12.
Figure 14:
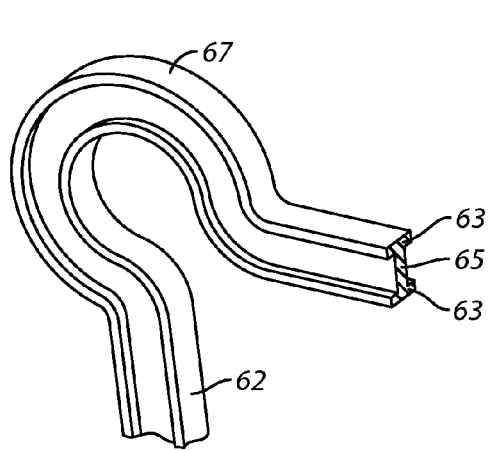
FIG. 14 is an enlarged fragmentary cross sectional view taken generally along line 14-14 of FIG. 13.
Figure 15:
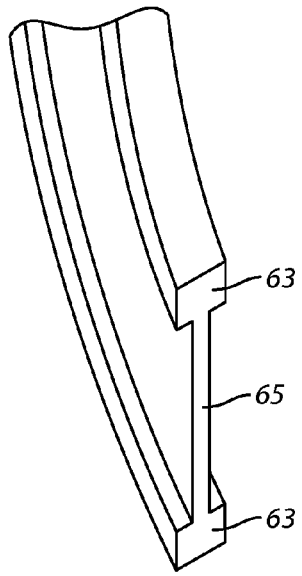
FIG. 15 is a fragmentary view enlarged in size of the pointed end of one leg of the staple shown in FIG. 13.

Although the staple 11 is shown as being formed from wireform material of circular cross-section, it could have other cross-sections. If, for example, it were desired to provide such a staple with greater rigidity, a staple 61 might be constructed in the form shown in FIGS. 12-15, having two legs 62 connected at their upper ends by a crown connector that includes a straight central connecting section 66, from wireform material having a cross-section of the general geometry of that of an I-beam. The wire material would be oriented (e.g. see FIG. 14) so that the two parallel flanges 63 that flank the central web 65 in the cross-section shape are oriented perpendicular to the plane of the staple 61. The thickness of the web 65 preferably does not differ from that of the flanges 63 by more than 25%. The length of the web 65 is preferably within 50% of the length of the flanges. More preferably the web is longer, and most preferably it is slightly longer, e.g. 20 to 30% longer, than either of the two flanges which are commonly equal in thickness and length. The essentially planar staple 61 of FIG. 12 might be formed with a straight central connecting section 66, with or without ears 67. It should be seen that such an I-beam cross-section would provide the resultant planar staple 61 with increased rigidity as a consequence of the shape of the two parallel flanges 63 spaced apart by centrally located web 65.

Although the invention has been described with regard to certain preferred embodiments which constitute what the inventor believes to be the best mode for carrying out his invention, it should be understood that various changes and modifications, as would be obvious to one having ordinary skill in the art, may be made without departing from the scope of the invention, which is defined by the claims appended hereto. Particular features of the invention are emphasized in the claims which follow.

The invention claimed is:

1. A surgical stapling tool which comprises:
a main body which includes a handle portion,
an effector extending from said body which holds at least one surgical staple having two legs with pointed ends and a crown connector interconnecting the opposite ends of the legs,
said effector including a first mechanism for adjusting the distance between the pointed ends of the legs so they become spaced apart a precise desired distance that is one of several different distances while the distance between upper ends of the legs at the crown connector remains unchanged,
an actuator-indicator incorporated in said body for operating said first mechanism,
a second mechanism which causes the effector to implant the staple into body tissue or organ tissue so as to achieve a precise amount of constriction, which constriction is dependent upon the one of said several different precise spaced apart distances to which the pointed ends were adjusted, and
an actuator for causing said second mechanism to operate.

2. The stapling tool of claim 1 wherein said first mechanism applies force to the interior surfaces of the legs to spread the pointed ends of the legs further apart to achieve said precise desired distance which is greater than the distance between upper ends of the legs at the crown connector.

3. The stapling tool of claim 1 wherein the legs and the crown connector are coplanar and the legs each have a shallow curvature with concave interior surfaces of the legs facing each other.

4. The stapling tool of claim 1 wherein said second mechanism is designed to drive a staple formed of shape memory material directly into body or organ tissue in which the staple is being implanted.

5. The stapling tool of claim 1 wherein said second mechanism is designed to hold the crown connector of a staple made of non-shape memory metal alloy and drives the staple into the tissue in a manner so as to bend the legs and effect plastic deformation thereof into a constricting shape at the time of implantation into body or organ tissue by applying force to exterior surfaces of the legs.

6. In combination, the stapling tool of claim 5 and a plurality of surgical staples each of which comprises two legs having pointed free ends and a crown connector interconnecting the upper ends of said legs, said staples being essentially planar and formed completely of wireform material having an I-beam cross-section where two parallel flanges flank a central web, which flanges are oriented perpendicular to the plane of the staple.

7. The stapling tool of claim 1 wherein said effector is designed to hold a planar staple made from metal alloy wire having an I-beam cross section in the form of a web and two parallel flanges, with said I-beam flanges in each leg being aligned perpendicular to the plane of the staple.

8. A surgical stapling tool which comprises:
a main body that includes a handle portion
an effector extending from said body which holds at least one planar surgical staple having two legs with points at one end and a crown connector interconnecting the opposite ends of the legs which planar staple is made from metal alloy wire having an I-beam cross section which has a web between two flanges, with the I-beam flanges in each leg being aligned perpendicular to the plane of the staple,
said effector including a first mechanism for spreading the legs of said staple to adjust the distance between the pointed ends of the legs,
an actuator-indicator incorporated in said body for operating said first mechanism to change the distance between the pointed ends to one of several precise spaced-apart distances that are different and each greater than the distance between the upper ends of the legs at the crown connector,
a second mechanism which causes the effector to implant the staple into body tissue or organ tissue so as to achieve a precise amount of constriction, which constriction amount is dependent upon the particular precise, spaced-apart distance to which the pointed ends were adjusted, and
a trigger for causing said second mechanism to operate.

9. The stapling tool of claim 8 wherein said first mechanism applies force to interior surfaces of the legs.

10. In combination, the stapling tool of claim 8 and a plurality of surgical staples each of which comprises two legs having pointed free lower ends and a crown connector interconnecting the upper ends of said legs, said staples being essentially planar and formed completely of wireform material having an I-beam cross-section, where the two flanges are parallel and oriented perpendicular to the plane of the staple.

11. The combination of claim 10 wherein the two flanges of the staple are about equal in length and about equal in thickness.

12. The combination of claim 11 wherein the cross sectional shape of the web has a thickness within about 25% of the thickness of each flange and a length which is not more than about 50% greater in length than each flange.

13. A surgical stapling tool which comprises:
a main body which includes a handle portion,
an effector extending from said body which holds at least one surgical staple having two legs with pointed ends and a crown connector interconnecting the opposite ends of the legs, with the legs and the crown connector being coplanar,
said legs each being formed with a continuous arcuate shallow curvature with concave interior surfaces of the legs facing each other,
said effector including a first mechanism for adjusting the distance between the pointed ends of the legs so the pointed ends become spaced apart a precise desired distance that is one of several different distances,
an actuator-indicator incorporated in said body for operating said first mechanism,
a second mechanism which causes the effector to implant the staple into body tissue or organ tissue so as to achieve a precise amount of constriction, which constriction is dependent upon the one of said several different spaced apart distances to which the pointed ends were adjusted, and
an actuator for causing said second mechanism to operate.

14. The stapling tool of claim 13 wherein said first mechanism adjusts the distance between the pointed ends while the distance between upper ends of the legs at the crown connector remains unchanged.

15. The stapling tool of claim 13 wherein said first mechanism applies force to the interior surfaces of the legs to spread the pointed ends of the legs further apart to achieve said precise desired distance, which distance is greater than the distance between upper ends of the legs at the crown connector.

16. The stapling tool of claim 13 wherein said second mechanism is designed to drive a staple formed of shape-memory metal directly into the tissue in which it is being implanted.

17. The stapling tool of claim 13 wherein said second mechanism is designed to hold the crown connector of a staple made of non-shape memory metal alloy and to drive it into the tissue in a manner so as to bend the legs and effect plastic deformation into a constricting shape at the time of implantation into the tissue by applying force to exterior surfaces of the legs.

* * * * *